US 6,746,711 B2

(12) United States Patent
Crass et al.

(10) Patent No.: US 6,746,711 B2
(45) Date of Patent: Jun. 8, 2004

(54) POLYMERS WITH BIOCIDAL ACTION, PROCESS FOR THEIR PREPARATION AND THEIR USE

(75) Inventors: Gerhard Crass, Friedberg (DE); Uwe Falk, Bruchköbel (DE); Béla Iván, Budapest (HU); Gábor Erdödi, Csokakŏ (HU); Árpád Máthe, Budapest (HU)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/352,834

(22) Filed: Jan. 28, 2003

(65) Prior Publication Data

US 2003/0191264 A1 Oct. 9, 2003

(30) Foreign Application Priority Data

Jan. 29, 2002 (DE) .......................... 102 03 342
Jan. 13, 2003 (EP) ............................ 03000713

(51) Int. Cl.⁷ .................. B05D 5/10; A01D 25/00; C08F 220/10
(52) U.S. Cl. ................. 427/207.1; 528/422; 525/330.3; 525/330.6; 524/779; 524/784; 524/788; 424/405; 424/411
(58) Field of Search ........ 528/422; 525/330.3, 525/330.6; 524/779, 784, 788; 427/207.1; 424/405, 411

(56) References Cited

U.S. PATENT DOCUMENTS 6,251,967 B1    6/2001   Perichaud et al. .......... 523/122

FOREIGN PATENT DOCUMENTS

| DE | 199 21 894 | 11/2000 |
| DE | 199 21 904 | 11/2000 |
| DE | 100 62 355 | 6/2001 |
| DE | 100 22 406 | 11/2001 |
| WO | WO 01/16193 | 3/2001 |

OTHER PUBLICATIONS

English abstract for DE 19921894, Nov. 16, 2000.
English abstract for DE 19921904, Nov. 16, 2000.
English abstract for DE 10062355, Jun. 28, 2001.
English abstract for DE 10022406, Nov. 15, 2001.
English abstract for WO 01/16193, Mar. 8, 2001.

*Primary Examiner*—Samuel A. Acquah
(74) *Attorney, Agent, or Firm*—Richard P. Silverman

(57) ABSTRACT

Polymers with biocidal action, process for their preparation and their use

The invention relates to polymers consisting essentially of structural units of the formula (1)

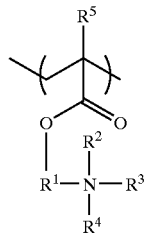

(1)

in which

R¹ is a $C_1$–$C_4$-alkylene group

R², R³ independently of one another, are a $C_8$–$C_{12}$-alkyl or alkenyl group R⁴ is methyl or ethyl R⁵ is hydrogen or methyl and whose molecular weight is between 1000 and 100 000 g/mol, to intermediates for their preparation, to a process for their preparation, and to their use as biocidal coating composition for surfaces and textiles.

13 Claims, No Drawings

POLYMERS WITH BIOCIDAL ACTION, PROCESS FOR THEIR PREPARATION AND THEIR USE

DESCRIPTION

The present invention relates to polymers of N,N,N-trialkylammoniumalkyl (meth)acrylates, to a process for their preparation and to their use for the biocidal finishing of surfaces or textiles.

For various reasons it may be necessary to give hard surfaces or textiles a biocidal finishing. This is intended to prevent microorganisms from being able to settle on said substrates and, more particularly, without repeated disinfection thereof using biocidal compositions.

Coating compositions for hard surfaces and textiles are known in principle.

Thus, DE-A-100 62 355 discloses copolymers for the coating of hard surfaces or of textiles which include anionic vinyl monomers and quaternary ammonium acrylates as comonomers. A biocidal action of such copolymers is not disclosed.

DE-A-199 21 894 discloses a process for the biocidal finishing of surfaces in which polymers of at least aliphatically monounsaturated monomers of the formula

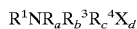

where $R^1$=H, branched, unbranched or cyclic, saturated or unsaturated hydrocarbon radical having up to 50 carbon atoms, which may be substituted by O, N or S atoms, $R^2$, $R^3$, $R^4$=H, branched, unbranched or cyclic saturated or unsaturated hydrocarbon radical having up to 25 carbon atoms, which may be substituted by O, N or S atoms, where $R^2$, $R^3$, $R^4$ are identical or different, X: an anion, a, b, c, d: in each case 0 or 1 are used. Examples of monomers containing quaternary nitrogen groups are 2-methacryloyloxyethyltrimethylammonium chloride, 2-methacryloyloxyethyltrimethylammonium sulfate, 3-methacryloylaminopropyltrimethylammonium chloride, N,N,N-trimethyl-3-(2-methyl-1-oxo-2-propenylamino)-1-propaneammonium chloride; N,N,N-triethyl-2-(1-oxo-2-propenylamino) ethaneammonium, N,N,N-trimethyletheneammonium bromide.

DE-A-199 21 904 discloses polymers which are suitable for the biocidal finishing of surfaces. These must be constructed from monomers which contain at least one quaternary amino group. The document names a series of suitable monomers with methyl, ethyl or benzyl substitution on the nitrogen atom.

It has been recognized that the polymeric coating compositions of the prior art are in need of improvement with regard to their biocidal action.

The object of the invention was therefore to discover novel polymers which can be applied to surfaces or textiles, and develop a biocidal action thereon.

Surprisingly, we have found that polymers of N,N,N-trialkylammoniumalkyl (meth)acrylates have these required properties if they carry long alkyl chains.

The invention therefore provides polymers consisting essentially of structural units of the formula (1)

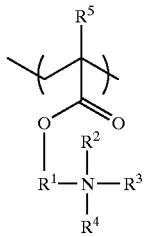

(1)

in which $R^1$ is a $C_1$–$C_4$-alkylene group $R^2$, $R^3$ independently of one another, are a $C_8$–$C_{12}$-alkyl or alkenyl group $R^4$ is methyl or ethyl $R^5$ is hydrogen or methyl and whose molecular weight is between 1000 and 100000 g/mol.

The invention further provides polymers consisting essentially of structural units of the formula (2)

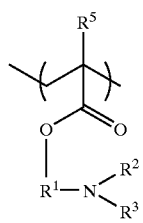

(2)

in which $R^1$, $R^2$, $R^3$ and $R^5$ have the meanings given above, and which have a molecular weight of from 1000 to 100000 g/mol.

The term "essentially" here means that the polymers according to the invention do not contain any other structural units which notably influence the properties of the polymers apart from those which conform to the formulae 1 and 2. It is assumed that the polymers can preferably comprise at most 2 mol %, in particular at most 0.5 mol %, of other structural units apart from formulae 1 and 2 without their properties being notably changed.

The polymers of the formula 1 can be prepared from the polymers of the formula 2 by quaternization. The polymers of the formula 2 therefore represent an intermediate for the polymers of the formula 1.

The invention further provides a process for the preparation of polymers of the formula 1 by reacting polymers of the formula 2 with a methylating or ethylating agent.

The invention further provides a process for the preparation of polymers of the formula 1 by transesterifying a (meth)acrylic alkyl ester, preferably a methyl ester, with a compound of the formula 3 to give the corresponding (meth)acrylic ester, then alkylating this transesterified product with a methylating or ethylating agent to give the quaternary ammonium compound, and subjecting this quaternary ammonium compound to free-radical polymerization.

The invention further provides a process for the preparation of polymers of the formula 2, by either A) reaction of a compound of the formula 3

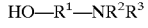

HO—$R^1$—$NR^2R^3$  (3)

with methyl (meth)acrylate in the presence of an esterification catalyst with removal of the methanol which forms during the reaction by distillation, and subsequent free-radical polymerizatioin of the resulting product,
or B) reaction of a methyl polymethacrylate with a compound of the formula 3 in the presence of an esterification catalyst with removal of the methanol which forms during the reaction by distillation.

The invention further provides for the use of polymers of the formula 1 for the biocidal finishing of surfaces and textiles.

$R^1$ is preferably an ethylene or propylene radical, in particular an ethylene radical.

$R^2$ and $R^3$ are preferably both the same radical. It is particularly preferred that $R^2$ and $R^3$ are octyl or decyl radicals, especially decyl radicals.

$R^4$ is preferably a methyl radical,
$R^5$ is preferably a methyl radical.

In a particularly preferred embodiment, the polymers according to the invention are those in which $R^1$=ethylene, $R^2$=$R^3$=decyl, $R^4$=$R^5$=methyl.

The molecular weights of the polymers of the formula 1 according to the invention are preferably between 2000 and 60000 g/mol, in particular between 5000 and 40000 g/mol.

The quaternization of the nitrogen atom both in the polymers according to formula 2 to give the polymers according to formula 1, and also in the monomers is preferably carried out using an alkyl sulfate, or an alkyl halide. Particular preference is given to dimethyl sulfate or methyl chloride.

The transesterification of the (meth)acrylic methyl ester with the compound of the formula 3 is preferably carried out in the presence of a basic esterification catalyst. Preferred catalysts are alkali metal hydroxides, alkali metal carbonates, alkaline earth metal hydroxides and organic tin compounds. Particular preference is given to $Sn(C_4H_9)_4$, $K_2CO_3$, KOH, $Ca(OH)_2$, NaOH, $NaOCH_3$, $Li_2CO_3$ and LiOH.

The free-radical polymerization of the compound obtained from a reaction of (meth)acrylic methyl ester and the compound of the formula 3 takes place by processes known in the prior art.

Suitable initiators for the process according to the invention are the initiators for free-radical polymerisations known in the prior art, preferably aziosobutyronitrile. The weight ratio of compounds of the formula 2 to the initiator is preferably less than 600:1, in particular less than 250:1.

The polymerization is preferably carried out at temperatures between 50 and 80° C., in particular 55 to 70° C. The at least single increase in the reaction temperature by at least 10° C. preferably takes place after 40% of the total reaction time, in particular up to 50% of the total reaction time.

The polymerization can be carried out in a solvent. Examples of suitable solvents are lower alcohols and lower alkylbenzenes, preferably methanol or toluene. The polymerization can also be carried out in the absence of solvents.

If a solvent is used, then the concentrations of the monomers are preferably about 30 to 50% by weight.

For use as a biocidal finishing agent, the polymer according to formula 1 in alcoholic and/or aqueous solution with a content of 1–50 g/l is applied to the surfaces and textiles to be treated. The polymers according to formula 1 are suitable in particular for the finishing of wool, polyester, polyamide and cotton.

EXAMPLES

A) Transesterification of Methyl Methacrylate (MMA) with Didecylaminoethanol (DDAE)

For the transesterification of MMA with DDAE, these substances were mixed with a catalyst and reacted at elevated temperature and reduced pressure. During the reaction, the methanol which forms was distilled off. The influence of the catalyst on the yield of the transesterification reaction is shown below (Table 1)

TABLE 1

Transesterification of MMA with DDAE

| Example | Catalyst | Yield, % |
|---------|----------|----------|
| 1 | $Al(iPrO)_3$ | ~0 |
| 2 | $Ti(PrO)_4$ | ~0 |
| 3 | $K_2CO_3$ | 12 |
| 4 | $K_2CO_3$ | 4 |
| 5 | $K_2CO_3$ | 4 |
| 6 | $Ca(OH)_2$ | 6 |
| 7 | $LiAlH_4$ | 50 |
| 8 | Dibutyltin maleate (DBTM) | 65 |
| 9 | DBTM | 51 |
| 10 | DBTM | 85 |
| 11 | DBTM | 57 |
| 12 | DBTM | 60 |
| 13 | $Sn(Bu)_4$ | 2 |
| 14 | $Sn(Bu)_4$ | 0 |
| 15 | $K_2CO_3$ (powder) | 2 |
| 16 | $K_2CO_3$ (powder) + PEG | 4 |
| 17 | KOH | 5 |
| 18 | $Ca(OH)_2$ | 1 |
| 19 | NaOH + PEG | 35 |
| 20 | NaOH | 36 |
| 21 | $NaOCH_3$ | ~0 |
| 22 | $Li_2CO_3$ | 3 |
| 23 | LiOH | 66 |
| 24 | LiOH + PEG | 68 |
| 25 | LiOH | 65 |
| 26 | LiOH | 72 |
| 27 | LiOH | 62 |
| 28 | LiOH | 68 |
| 29 | LiOH | 58 |
| 30 | LiOH | 55 |
| 31 | LiOH | 51 |
| 32 | LiOH | 62 |

B) Transesterification of Polymethyl Methacrylate (PMMA) with DDAE

The polymer-analogous transesterification was carried out like the monomeric reaction under A). The reactants were dissolved in toluene, and after the reaction the product was precipitated with methanol and dried under reduced pressure. RT means reaction temperature, RZ means reaction time.

TABLE 2

| Example | g of DDAE | g of PMMA | RT,° C. | RZ, h | Catalyst |
|---------|-----------|-----------|---------|-------|----------|
| 33 | 10.76 | 1.31 | 100 | 10 | KOH |
| 34 | 10.76 | 1.31 | 160 | 10 | $LiACH_4$ |
| 35 | 17.0 | 2.07 | 100 | 10 | Dibutyltin maleate |

C) Quaternization of the DDAEMA

Example 36

300 g of DDAEMA were heated to 75° C. in an autoclave. Methyl chloride was injected to a pressure of 4 bar. The pressure was maintained at 4 bar by topping up. After a reaction time of 6 h, the autoclave was decompressed and the excess methyl chloride was removed under reduced pressure. This gave 320 g of the quaternized product. The degree of quaternization was 95%

Example 37

100 g of DDAEMA were heated to 40° C. Over the course of 15 minutes, 31 g of dimethyl sulfate were added dropwise and the reaction mixture was stirred for a further 10 h at 40° C. This gave 125 g of the quaternized product. The degree of quaternization was 97%

D) Polymerization of the Didecylaminoethyl Methacrylate (DDAEMA)

The polymerization of the DDAEMA was triggered by mixing this material with AIBN as free-radical initiator and subsequent degassing under reduced pressure. The polymerization was carried out under an argon atmosphere, and the product was precipitated with methanol.

TABLE 3

| Example | DDAEMA from Example | RT, ° C. | RZ, h |
|---------|---------------------|----------|-------|
| 38 | 8.5 g from Example 1 | 75 | 6 |
| 39 | 56.2 g from Example 12 | 75 | 2 |

E) Preparation of Quaternized Poly-N,N-didecylaminoethyl Methacrylate

1. Preparation of N,N-Didecylaminoethyl Methacrylate (DDAEMA) (Corresponds to Example 32)

257.4 g of DDAE, 1.508 g of phenothiazine and 736.4 mg of LiOH were stirred in a heated reaction vessel for 30 minutes under a nitrogen atmosphere at atmospheric pressure. 150.7 g of MMA (two-fold molar excess) were then added at a batch temperature of 90° C. 30 minutes later, the temperature of the reaction was increased to 104° C. and distillation of the methanol which formed was started. The pressure was reduced to 126 Torr over the course of 60 min, later to 24 Torr. MMA which remained was distilled off at this pressure. This gave 292.5 g of DDAEMA.

Inhibitor and LiOH were removed from the distillation residue with 20 g of $Al_2O_3$. The product was purified over the course of 1 day over an $Al_2O_3$ chromatography column without pressure.

2. Polymerization of the DDAEMA to Poly-DDAEMA

Example 40

50 g of the product from Example 32 (comprises 35.5 g of DDAEMA), 142 g of AIBN and 50 $cm^3$ of hexane were mixed in a reaction vessel. The solution was cooled to −20° C., and argon was passed through for 15 min. To trigger the polymerization, the temperature was then increased to 65° C. 16 hours later, the reaction mixture was cooled to room temperature, and the product was precipitated in 1 l of methanol. The precipitation was then taken up in 200 ml of hexane and precipitated again with 500 ml of methanol. The polymer obtained in this way was dissolved in 200 ml of hexane and extracted with water in order to remove methanol residues. The hexane solution was then dried over $CaCl_2$ and filtered and the hexane was stripped off. This gave 24.3 g of poly-DDAEMA.

3. Quaternization of the Poly-DDAEMA

To quaternize the poly-DDAEMA, a known amount of 14 g, dissolved in hexane, of the product from Example 40 were removed and diluted with 20 ml of hexane or 10 ml of hexane and 20 mol of isobutanol. The reaction vessel was then placed in an isopropanol/dry ice bath, and a solution of dimethyl sulfate in isobutanol was added. The reaction temperature was maintained at about 20° C. After the reaction, the solvents were stripped off and the quaternized polymer was isolated and dried.

Example 47

40 g of the poly-DDAEMA were dissolved in 217 g of n-hexane and 10 g of isopropanol and heated to 60° C. Over the course of 15 minutes, 12.3 g of dimethyl sulfate were added dropwise and the reaction mixture was stirred for a further 10 h at 60° C. The solvents were distilled off under reduced pressure, giving 48 g of the quaternized polymer. The degree of quaternization was 97%

Example 48

38 g of the poly-DDAEMA were dissolved in 195 g of n-hexane and 10 g of isopropanol and heated to 66° C. in an autoclave. Methyl chloride was injected to a pressure of 4 bar. The pressure was maintained at 4 bar by topping up. After a reaction time of 6 h, the autoclave was decompressed and the excess methyl chloride and the solvents were removed under reduced pressure. This gave 35 g of the quaternized polymer. The degree of quaternization was 95%

TABLE 4

Quaternization of poly-DDAEMA

| Example | Amount of poly-DDAEMA, g | Amount of quat. g | Degree of quaternization, % | Reaction time, min |
|---------|--------------------------|-------------------|-----------------------------|--------------------|
| 41 | 14.089 | 3.04 | 100 | 40 |
| 42 | 13.357 | 3.004 | 100 | 60 |
| 43 | 14.196 | 3.018 | 82 | 20 |
| 44 | 13.82 | 2.847 | 63 | 15 |
| 45 | 13.258 | 2.589 | 44 | 15 |
| 46 | 13.271 | 2.508 | 22 | 28 |
| 47 | 40 | 48 | 97 | 615 |
| 48 | 38 | 35 | 95 | 360 |

F) Polymerization of the Quaternized DDAEMA

Example 49

50 g of the product from Example 36 (comprises 47.5 g of methyl-quaternized DDAEMA), 145 g of AIBN and 55 $cm^3$ of hexane were mixed in a reaction vessel. The solution was cooled to −20° C., and argon was passed through for 15 min. To trigger the polymerization, the temperature was then increased to 65° C. 16 hours later, the reaction mixture was cooled to room temperature and the product was precipitated in 1 l of methanol. The precipitation was then taken up in 200 ml of hexane and precipitated again with 500 ml of methanol. The polymer obtained in this way was dissolved in 200 ml of hexane and extracted with water in order to remove methanol residues. The hexane solution was dried over $CaCl_2$ and filtered, and the hexane was stripped off. This gave 26.8 g of poly(methyl-quaternized) DDAEMA.

The biocidal action of the quaternized polymers according to the invention was determined using the shake-flask method.

This test method serves for the quantitative determination of the antibacterial action of nondiffusing active ingredients. Compared with others, the method has the advantage that it ensures good contact between bacteria and finished substrate. Fibers and fabrics are suitable for the investigation.

The test samples of 0.75 g are placed into a 100 ml Pyrex flask with 70 ml of sterile buffer solution. The buffer solution used is a solution of 3.4 g of $KH_2PO_4$ in 100 ml of $H_2O$ which has been adjusted to pH 7.2 with NaOH. This working solution is diluted 1:800.

For the test, the buffer solution is treated with 5 ml of inoculum and briefly shaken. To prepare the inoculum, the day culture is diluted with buffer solution such that the end concentration is about $1-3 \times 10^5$ CFU/ml (colony forming units/ml).

The number of microbes per ml for 0 hour is determined from one flask, by plating out ($10^1$, $10^{-1}$, $10^{-2}$, $10^{-3}$) on TSA (Trypticase Soy Agar).

The flasks are shaken for 24 hours at room temperature on a shaker. Then, from each flask, the number of microbes per ml is determined for 24 hours, by plating out ($10^1$, $10^{-1}$, $10^{-2}$, $10^{-3}$) on TSA. The procedure is as above at 0 hours.

The assessment takes place by counting out the "colony forming units" after 0 hours and after a shaking time of the samples of 24 hours. The resulting figures of the colony forming units (CFU) are given in logarithmic form and calculated in accordance with the following formula:

log (reduction)=(log CFU/ml after 0 hours contact time)−(log CFU/ml after 24 hours contact time)

The evaluation of the result is as follows:

| | |
|---|---|
| log reduction <0.0 | no antibacterial action |
| log reduction 0.1–1.0 | bacteriostatic action |
| log reduction 1.1–2.0 | bactericidal action |
| log reduction >2.0 | significant bactericidal action |

The day culture used was *Staphylococcus aureus* ATCC 6538.

TABLE 5

Effectiveness of the quaternized poly-DDAEMA according to the invention

| Example | Sample | quat. poly-DDAEMA | log (reduction) |
|---|---|---|---|
| 50 | without | — | −0.2 |
| 51 | cotton | 0 | −0.1 |
| 52 | cotton | 10 | −0.2 |
| 53 | cotton | 20 | 0.9 |
| 54 | wool | 20 | 2.1 |
| 55 | wool | 20 | >4.3 |
| 56 | polyester | 10 | >4.3 |
| 57 | polyester | 20 | >4.3 |
| 58 | polyamide | 10 | 4.0 |
| 59 | polyamide | 20 | >4.3 |

What is claimed is:

1. A method for biocidal finishing of surfaces and/or textiles comprising applying to said surfaces/textiles a polymer consisting essentially of structural units of the formula 1.

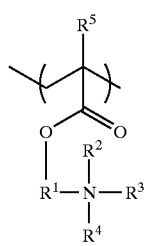

(1)

in which
$R^1$ is a $C_1$–$C_4$-alkylene group
$R^2$, $R^3$ independently of one another, are a $C_8$–$C_{12}$-alkyl or alkenyl group
$R^4$ is methyl or ethyl
$R^5$ is hydrogen or methyl
and whose molecular weight is between 1000 and 100 000 g/mol.

2. The method of claim 1, in which $R^1$ is an ethylene or propylene radical.

3. The method of claim 1, in which $R^2$ and $R^3$ are both octyl or decyl radicals.

4. The method of claim 1, in which $R^4$ is a methyl radical.

5. The method of claim 1, in which $R^5$ is a methyl radical.

6. The method of claim 1, in which the molecular weight of the polymers is between 2000 and 60 000 g/mol.

7. A process for the preparation of a polymer consisting essentially of structural units of the formula 2

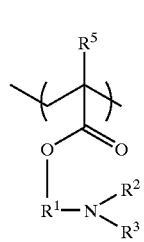

(2)

in which
$R^1$ is a $C_1$–$C_4$-alkylene group
$R^2$, $R^3$ independently of one another, are a $C_8$–$C_{12}$-alkyl or alkenyl group
$R^4$ is methyl or ethyl
$R^5$ is hydrogen or methyl
said polymer having a molecular weight of from 1000 to 100 000 g/mol, comprising either:
A) esterifying a compound of the formula 3

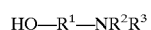

HO—$R^1$—$NR^2R^3$ (3)

with (meth)acrylic alkyl esters in the presence of an esterification catalyst to form an esterified product and an alkanol, removing the alkanol by distillation, and polymerizing by free-radical polymerization of the esterified product to provide the polymer, or B) esterifying a polymethacrylic alkyl ester with a compound of the formula 3 in the presence of an esterification catalyst to form an esterified product and an alkanol, removing the alkanol to provide the polymer.

8. The process as claimed in claim 7, where the esterification catalyst is selected from the group consisting of alkali metal hydroxides, alkali metal carbonates, alkaline earth metal hydroxides, organic tin compounds, titanium compounds and mixtures thereof.

9. A process for the preparation of a polymer consisting essentially of structural units of formula 1

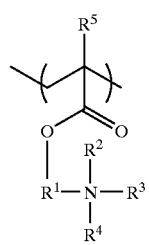

(1)

in which $R^1$ is a $C_1$–C4-a alkylene group $R^2$, $R^3$ independently of one another, are a $C_8$–$C_{12}$-alkyl or alkenyl group $R^4$ is methyl or ethyl (2)

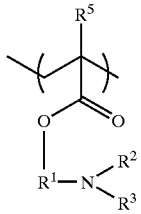

in which $R^1$ is a $C_1$–$C_4$-alkylene group $R^2$, $R^3$ independently of one another, are a $C_8$–$C_{12}$-alkyl or alkenyl group $R^4$ is methyl or ethyl $R^5$ is hydrogen or methyl with a methylating or ethylating agent.

10. A process for the preparation of polymers of the formula 1

(1)

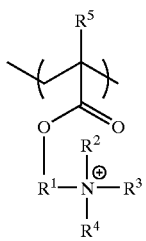

in which $R^1$ is a $C_1$–$C^4$-alkylene group $R^2$, $R^3$ independently of one another, are a $C_8$–$C_{12}$-alkyl or alkenyl group $R^4$ is methyl or ethyl $R^5$ is hydrogen or methyl comprising;

a) transesterifying a compound of the formula 3

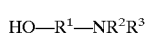 (3)

to give a transesterified product comprising a corresponding (meth)acrylic ester, b) quaternizing or alkylating the transesterified product with a methylating or ethylating agent to provide a quaternary ammonium compound, and c) polymerizing the quaternary ammonium compound by free-radical polymerization of the resulting quaternary ammonium compound to provide the polymer.

11. A polymer consisting essentially of structural units of the formula (1)

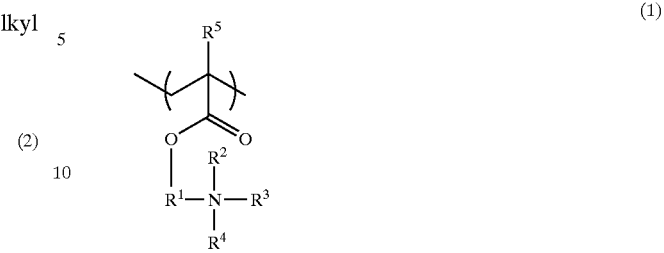

in which $R^1$ is a $C_1$–$C_4$-alkylene group $R^2$, $R^3$ independently of one another, are a $C_8$–$C_{12}$-alkyl or alkenyl group $R^4$ is methyl or ethyl $R^5$ is hydrogen or methyl and whose molecular weight is between 1000 and 100 000 g/mol.

12. A polymer consisting essentially of structural units of the formula (2)

in which $R^1$ is a $C_1$–$C_4$-alkylene group $R^2$, $R^3$ independently of one another, are a $C_8$–$C_{12}$, -alkyl or alkenyl group $R^4$ is methyl or ethyl $R^5$ is hydrogen or methyl and said polymer having a molecular weight of from 1000 to 100 000 g/mol.

13. A compound of the formula 5

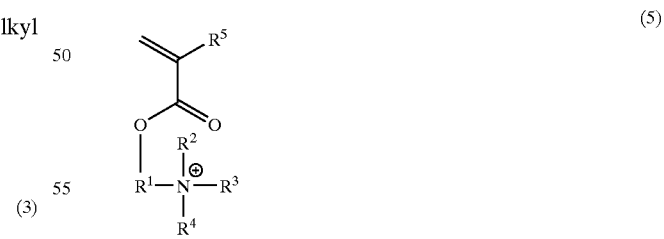

in which $R^1$ is a $C_1$–$C_4$-alkylene group $R^2$, $R^3$ independently of one another, are a $C_8$–$C_{12}$-alkyl or alkenyl group $R^4$ is methyl or ethyl $R^5$ is hydrogen or methyl.

* * * * *